United States Patent
Eiler et al.

(10) Patent No.: US 10,115,577 B1
(45) Date of Patent: Oct. 30, 2018

(54) ISOTOPE RATIO MASS SPECTROMETRY

(71) Applicants: Thermo Fisher Scientific (Bremen) GmbH, Brenmen (DE); California Institute of Technology, Pasadena, CA (US)

(72) Inventors: John Eiler, Sierra Madre, CA (US); Jens Griep-Raming, Ganderkesee (DE)

(73) Assignees: California Institute of Technology, Pasadena, CA (US); Thermo Fisher Scientific (Bremen) GmbH, Bremen (DE)

( * ) Notice: Subject to any disclaimer, the term of this patent is extended or adjusted under 35 U.S.C. 154(b) by 0 days.

(21) Appl. No.: 15/697,612

(22) Filed: Sep. 7, 2017

(51) Int. Cl.
| | | |
|---|---|---|
| *H01J 49/02* | (2006.01) | |
| *H01J 49/42* | (2006.01) | |
| *H01J 49/06* | (2006.01) | |
| *B01D 59/44* | (2006.01) | |
| *G01N 30/02* | (2006.01) | |
| *G01N 30/88* | (2006.01) | |

(52) U.S. Cl.
CPC ......... *H01J 49/025* (2013.01); *H01J 49/063* (2013.01); *H01J 49/4215* (2013.01); *H01J 49/4225* (2013.01); *B01D 59/44* (2013.01); *G01N 2030/025* (2013.01); *G01N 2030/8868* (2013.01)

(58) Field of Classification Search
CPC ........ G01N 1/405; G01N 1/10; G01N 1/2202; G01N 1/44; G01N 30/128; G01N 30/12; G01N 30/24; G01N 30/14; G01N 30/30; G01N 30/40; G01N 30/461; G01N 30/6078; G01N 30/66; G01N 30/7206; G01N 30/80; G01N 30/82; G01N 30/88; G01N 31/12; G01N 2030/121; G01N 2030/125; G01N 2030/143; G01N 2030/8804; G01N 2030/8886; G01N 27/70; H01J 49/0422; H01J 49/168; H01J 49/0013; H01J 49/0031; H01J 49/005; H01J 49/045; H01J 49/0495; H01J 49/10; H01J 49/145; H01J 49/24; H01J 49/26
USPC ..................... 250/288, 282, 287, 324, 423 R
See application file for complete search history.

(56) References Cited

U.S. PATENT DOCUMENTS

| | | | | | |
|---|---|---|---|---|---|
| 2,951,361 | A | * | 9/1960 | Fuller ................... | G01N 30/88 73/23.4 |
| 3,267,646 | A | * | 8/1966 | Kauss ................... | G01N 30/80 137/625.41 |
| 3,366,149 | A | * | 1/1968 | Taft ....................... | G01N 30/24 141/329 |
| 3,408,793 | A | * | 11/1968 | Frazer ................... | G01N 30/24 73/864.81 |

(Continued)

*Primary Examiner* — David A Vanore
(74) *Attorney, Agent, or Firm* — Sage Patent Group (57) ABSTRACT

Isotope ratio mass spectrometry is effected by: injecting a sample for analysis into a gas chromatography column; directing an effluent from the gas chromatography column to a switching arrangement; and selecting a configuration of the switching arrangement, such that: in a first mode, the effluent from the gas chromatography column is provided as an input to a peak broadener; and in a second mode, an effluent from the peak broadener is provided to a mass spectrometer for isotope ratio mass spectrometry without the effluent from the gas chromatography column being provided as an input to the peak broadener.

27 Claims, 8 Drawing Sheets

(56) References Cited

U.S. PATENT DOCUMENTS

| | | | | |
|---|---|---|---|---|
| 3,847,546 | A * | 11/1974 | Paul | G01N 30/12 |
| | | | | 422/78 |
| 5,955,886 | A * | 9/1999 | Cohen | G01N 27/70 |
| | | | | 250/324 |
| 8,502,140 | B2 * | 8/2013 | Whitehouse | H01J 49/045 |
| | | | | 250/282 |
| 8,785,846 | B2 * | 7/2014 | Ouyang | H01J 49/0013 |
| | | | | 250/288 |
| 9,389,244 | B2 * | 7/2016 | Goeckeritz | G01Q 70/14 |
| 9,768,002 | B2 * | 9/2017 | Campbell | H01J 49/005 |
| 2010/0281950 | A1 * | 11/2010 | Weres | G01F 15/08 |
| | | | | 73/31.07 |
| 2011/0201126 | A1 * | 8/2011 | Hughes | H01J 49/0422 |
| | | | | 436/175 |
| 2017/0284978 | A1 * | 10/2017 | Cardin | B01L 3/502 |

* cited by examiner

ISOTOPE RATIO MASS SPECTROMETRY

TECHNICAL FIELD

The present disclosure concerns a method of Isotope Ratio Mass Spectrometry (IRMS) and an isotope ratio mass spectrometry system. The method and system both use gas chromatography.

BACKGROUND

Historically, accurate and precise isotope ratios have been measured using magnetic sector-type instruments. Orbital trapping mass spectrometers, such as the Orbitrap™ mass analyzer manufactured by Thermo Fisher Scientific, Inc., have more recently been shown able to provide accurate and precise isotope measurements ("The 100 isotopologue challenge: Orbitrap mass spectrometry as a means of high-dimension clumped and position-specific isotope analysis", John Eiler, Brooke Dallas, Elle Chimiak, Johannes Schwieters, Dieter Juchelka, Alexander Makarov, Jens Griep-Raming, Poster at ASMS 2016). However, the precision that can be obtained is limited by the number of ions detected, which in turn is limited by the space charge capacity of the ion optical storage elements involved in the mass spectrometer, for example the linear ion trap (C-trap) used for storing ions for injection into the Orbitrap™ mass analyzer. For transient signals, such as from chromatographic separation, typically only a very small fraction of the total number of ions generated in the ion source can be practically used.

For each measurement scan of ions in an orbital trapping mass analyzer, a transient is acquired for several milliseconds (referred to as a detection time, DT). For most applications under consideration, DT is in the order of 250 ms, 500 ms, or even longer. Whilst detection in the orbital trapping mass analyzer is taking place, ions can be collected and stored in an ion storage device for analysis in the next measurement scan. If the ion storage time (IT) is equally long or longer than DT, in general nearly all of the stored ions can be analyzed. Experimental overhead times, such as the time from stopping the ion collection process to injection into the mass analyzer, normally cannot be avoided and therefore modify this calculation slightly. These times are typically negligible compared to an overall cycle time though. However, when chromatographic separation of the sample is used, for instance using a gas chromatograph (GC), IT is usually significantly shorter than DT and it may not then be possible to achieve a sufficient number of scans in the mass analyzer. The result of this may be loss of a significant fraction of the ions produced and consequent reduced overall precision and accuracy of the measured isotope ratios.

Such problems are even more significant for orbital trapping mass analyzers, in which the total number of ions that can be observed in each injection may be limited by space charge effects. No matter how scans are organized, there is a limit in the number of ions observed per second for such analyzers, which cannot be exceeded. This limit may be as a low as $2 \times 10^4$ to $3 \times 10^4$ ions per second. A typical GC peak lasts a few seconds, so in direct elution of peaks, it may not be possible to observe more than $2 \times 10^5$ to $3 \times 10^5$ ions. Often, $10^7$ to $10^8$ ions per measurement must be reached, in order to achieve desirable shot noise limits for common isotopic analyses.

Figure 1:
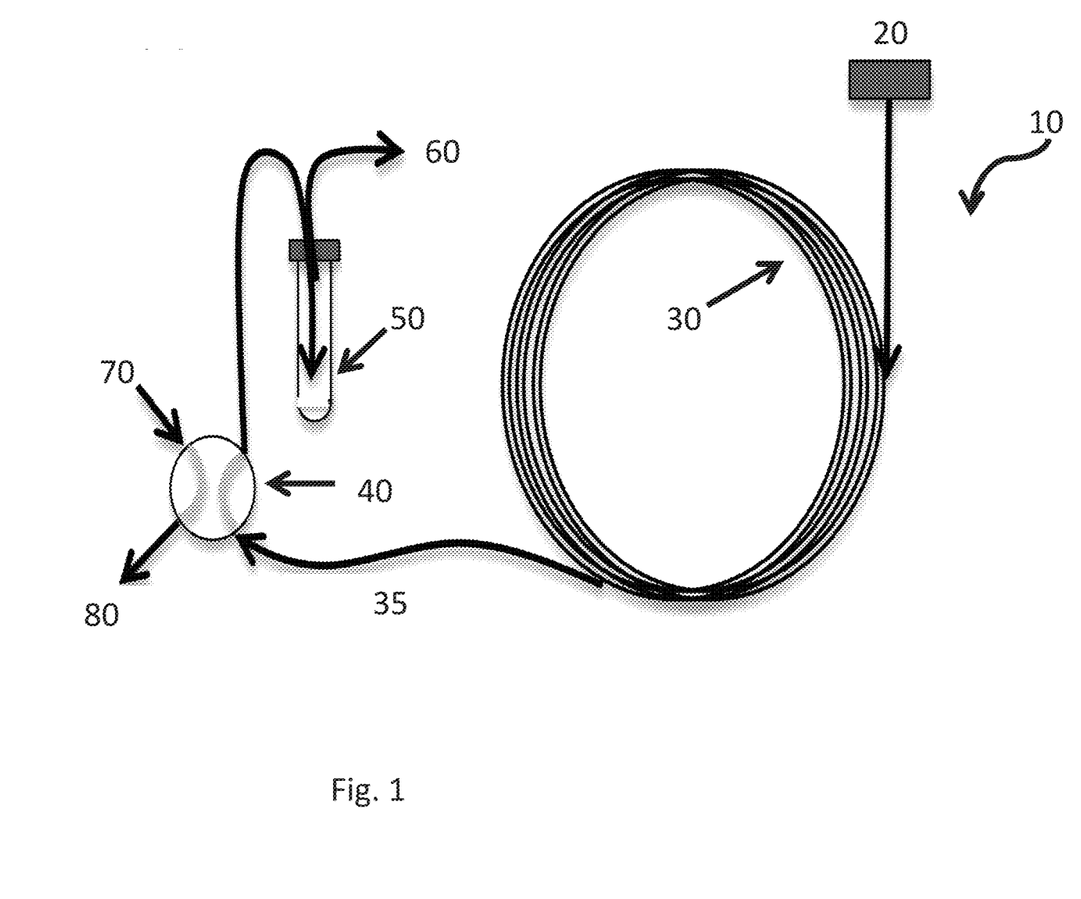
FIG. 1 schematically shows a known isotope ratio mass spectrometry system with a peak broadening device in-line with a GC column, operated by a single in-line valve.

These issues can be addressed with the use of a peak broadening device in-line with a GC column, such as described in the above reference and in a presentation at Clumped Isotope Workshop, January 2016 by John Eiler et al. With reference to FIG. 1, there is schematically shown a known IRMS system with such a peak broadening device in-line with a GC column, operated by a single in-line valve. The IRMS system 10 comprises: an injector 20; a GC column 30; a multi-port switching valve 40; and a peak broadener 50. The injector 20 provides sample input to the GC column 30. The column flow 35 from GC column 30 is provided as a first input to the multi-port switching valve 40. A second input to the multi-port switching valve 40 is coupled to a helium supply 70. A first output of the multi-port switching valve 40 is provided as an input to the peak broadener 50. The output of the peak broadener 50 is provided to the ion source of the mass spectrometer 60, such that the peak broadener 50 is provided in line between the GC column 30 and the mass spectrometer 60. The mass spectrometer 60 is preferably an orbital trapping mass analyzer. The peak broadener 50 can be in the form of a tube or flask. A second output of the multi-port switching valve 40 is provided to a vacuum pump acting as a vent or waste line 80.

This allows the column flow 35 to be provided to the peak broadener 50 and mass spectrometer 60 when a compound (peak) of interest is output, or to be passed to a vent at other times. It can thereby extend the time available for mass spectrometry analysis of sample peaks eluting from the column. As an example, such devices may make peaks last hundreds of seconds (minutes to tens of minutes) to reach desired analytical goals. In this way, a mass analysis of the compound or compounds of interest can be performed without a significant reduction in the number of ions lost (conversely, improving the useful ion yield in the analysis). However, further improvements to the precision and accuracy of isotope ratio measurements using this technique would be desirable.

SUMMARY

Against this background, there is provided a method of isotope ratio mass spectrometry in accordance with claim 1 and an isotope ratio mass spectrometry system as defined in claim 17. Further features of the inventive concepts are detailed in the dependent claims.

A switching arrangement is used that can select between a first mode, in which effluent from the gas chromatography column is provided as an input to a peak broadener and a second mode, where an effluent from the peak broadener is provided to a mass spectrometer for isotope ratio mass spectrometry. In particular, this second mode is effected without the effluent from the gas chromatography column being provided as an input to the peak broadener. This allows the path from the GC column to the peak broadener to be separately controlled from the path from the peak broadener to the mass spectrometer. Advantageously, the first mode can be used when the effluent from the gas chromatography column comprises a compound of interest, for example a peak that is desired to be subject to isotope ratio analysis using the mass spectrometer, especially with high precision and accuracy. Conversely, some embodiments use the second mode when the effluent from the gas chromatography column does not comprise a compound of interest. Then, the effluent from the gas chromatography column may be provided to a waste line for disposal, in the second mode. Moreover, a buffer gas (such as helium) may be provided as an input to the peak broadener in the second mode. This may help to avoid contamination in the peak broadener.

Existing configurations, such as shown in FIG. 1, provide a fixed in-line peak broadener, which results in all peaks from the GC column being broadened and then immediately mass analyzed. It has been recognized that the in-line design of the peak broadener does not allow direct observation of the chromatogram and proper timing of the valve switching. This makes such configurations difficult to operate. Moreover, for the peak broadener to be effective, a peak of interest eluting from the GC column is desirably separated in time from any peaks of other compounds, preferably by approximately 1 minute or more. This is not always possible, especially for analytes that are introduced to the injector as components of complex mixtures, and therefore limits the usefulness of the peak broadener. In addition, it has been found that this existing configuration does not permit observation of two or more peaks of a single chromatogram, as the only path to the ion source is through the peak broadener. Thus, all peaks other than the one chosen for trapping in the peak broadener are discarded.

Decoupling the paths between the GC column and the peak broadener and between the peak broadener and the mass spectrometer, using the switching arrangement, allows greater flexibility in the way in which the peaks eluting from the GC column are handled and thereby addresses these issues. The first and second mode may allow peak broadening of the eluted peaks. In addition, a third mode of the switching arrangement may provide the effluent from the gas chromatography column to the mass spectrometer for isotope ratio mass spectrometry without passing through the peak broadener (in particular, directly). Thus, some peaks may be switched and sent directly to the mass spectrometer through a bypass line, without peak broadening. This may be used in an initial analysis step, particularly to determine a retention time and/or peak width for a compound of interest. Then, the selection of the first mode (especially its timing) in a subsequent analysis step can be based on the determined retention time and/or peak width.

This method is especially useful when a mass analyzer is being used that has a detection time that is longer and preferably significantly (at least 2, 3, 5, 10, 100, 500 or 1000 times) longer than the ion storage time. In other words, this method is useful where the mass spectrometer comprises an ion storage device for collecting and storing ions prior to ejecting them for analysis in the next measurement in the mass analyzer. For example, this may be the case for an electrostatic Fourier Transform Mass Spectrometry (FTMS) mass analyzer and in particular, an orbital-trapping type mass analyzer.

The switching arrangement beneficially comprises multiple switching devices, each of which may be a multi-port switching valve or a Deans' switch configuration, for instance. Then, the first switching device may receive the effluent from the gas chromatography column as a first input and a buffer gas source as a second input. Its first output may be coupled to the input of the peak broadener. Its second output may be provided as a first input to a second switching device. The second switching device's second input may be an output of the peak broadener, its first output may be coupled to a sample input of the mass spectrometer (the ion source) and its second output may be coupled to a waste line (such as a vacuum pump).

A number of optional additional features can also be considered. A partial pressure of the effluent from the peak broadener may be stabilized, for instance by one of: adjusting a volume of the peak broadener (using a bellows device, a syringe, or gas-filled balloon within the peak broadener, for example); compensating for a partial pressure loss by filling part (that is, not all) of the reservoir volume with a liquid and/or increasing gas flow into the reservoir volume; and increasing a temperature of the reservoir volume to expand gas in the peak broadener and/or increasing the total pressure inside the peak broadener. A reservoir volume of the peak broadener may have an internal surface (walls) with a deactivation coating and/or may be at least partly defined by a metal surface coated with a glass-like microcoating.

The peak broadener could be a tube or flask. Alternatively, it may comprise: a gas trap first stage; and a controlled desorption second stage. A rate of desorption in the second stage may be controlled to effect a desired (preferably constant) partial pressure of effluent from the peak broadener. For example, the second stage may be a thermal desorption arrangement (the rate being controlled by temperature) or the second stage may be directed gas flow desorption arrangement (the rate being set by controlling a gas flow).

In some embodiments, a second peak broadener can be used, with the switching arrangement further configured to decouple the paths between the GC column and the second peak broadener and between the second peak broadener and the mass spectrometer. Three or more peak broadeners can be used in additional embodiments.

BRIEF DESCRIPTION OF THE DRAWINGS

The inventive concepts may be put into practice in a number of ways, and a preferred embodiment will now be described by way of example only and with reference to the accompanying drawings, in which.

DETAILED DESCRIPTION OF EMBODIMENTS

Figure 2:
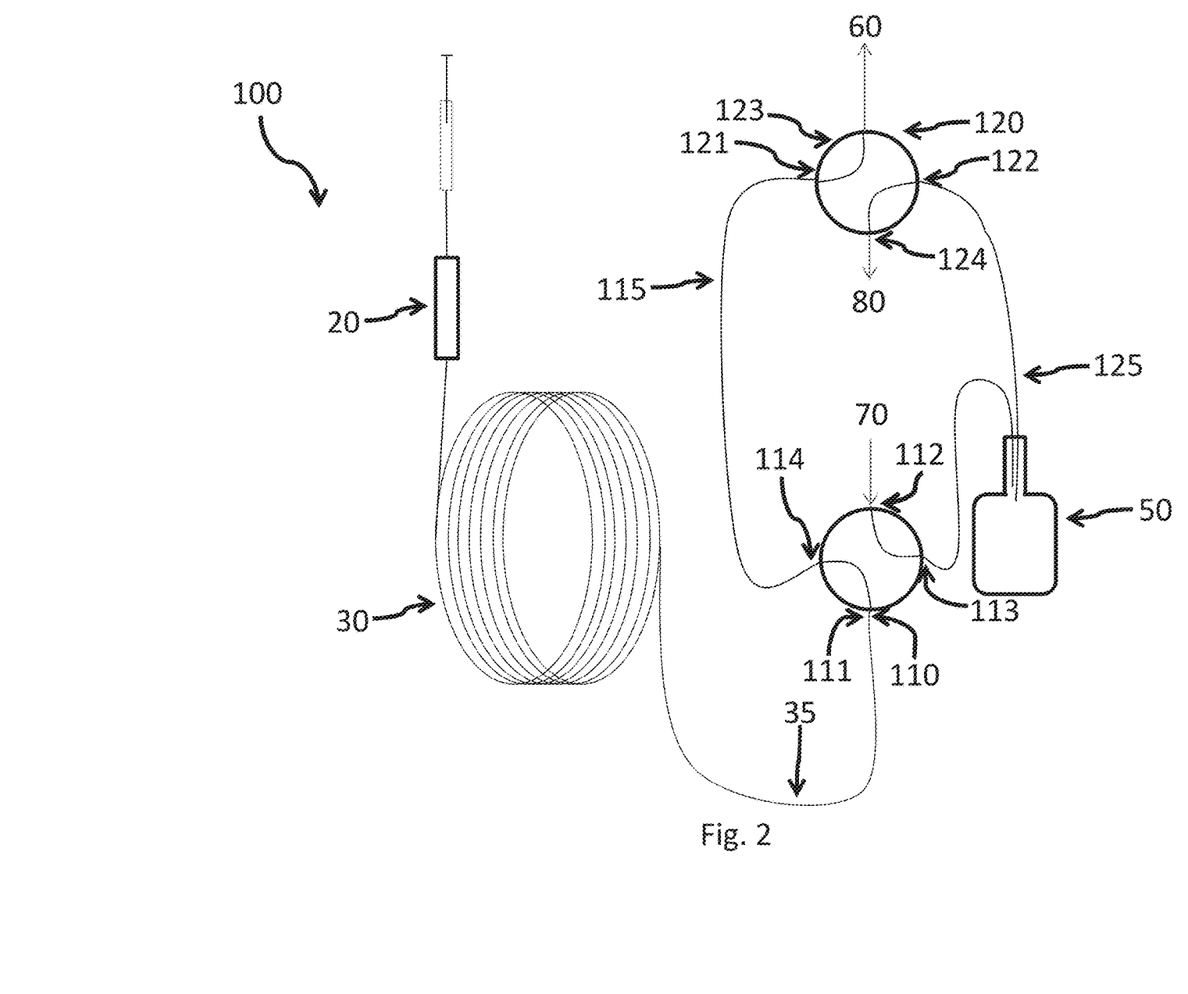
FIG. 2 depicts a schematic of an isotope ratio mass spectrometry system in accordance with a first embodiment of the disclosure, in a first configuration.

Referring first to FIG. 2, there is depicted a schematic of an Isotope Ratio Mass Spectrometry (IRMS) system in accordance with a first embodiment of the disclosure, in a first configuration. The IRMS system 100 has some features common with those of the existing IRMS shown in FIG. 1. Where the same features are indicated, identical reference numerals have been used.

The IRMS system 100 comprises: an injector 20; a GC column 30; a first multi-port switching valve 110; a second multi-port switching valve 120; and a peak broadener 50. The sample is introduced to the injection port of the GC column 30 using a gas or liquid syringe (injector 20). The injector 20 provides sample input to the GC column 30, which is typically housed in an oven (not shown). The column flow 35 from GC column 30 (the distal end of the GC column 30) is provided as a first input 111 to the first multi-port switching valve 110. A second input 112 to the first multi-port switching valve 110 is coupled to a helium gas stream 70. A first output 113 of the first multi-port switching valve 110 is provided as an input to the peak broadener 50. A second output 114 of the first multi-port switching valve 110 is provided by a capillary 115 (a bypass line) directly as a first input 121 to a second multi-port switching valve 120.

The output of the peak broadener 50 is provided (the peak broadener 50 is drained) through a second capillary 125 as a second input 122 to the second multi-port switching valve 120. A first output 123 of the second multi-port switching valve 120 is provided via a transfer line to the ion source of the mass spectrometer 60. A second output 124 of the second multi-port switching valve 120 is provided to a vacuum pump acting as a waste line 80. The mass spectrometer 60 is preferably an orbital trapping mass analyzer.

The peak broadener 50 is in the form of a tube or flask, for example having a 20 cc glass volume. The volume of the peak broadener 50 is selected to match the precision requirements of the analysis, that is, to match with the total time of analysis required to achieve the desired isotope ratio precision. It has been found that a volume of about 1 mL broadens GC peaks to about 50-60 seconds (at typical carrier gas flow settings of around 1 mL/m in) or a volume of about 20 mL results in peak widths of about 50-60 minutes.

Rather than providing the peak broadener 50 in line between the GC column 30 and the mass spectrometer 60, this configuration allows trapping of a peak eluted from the GC column 30, followed by analysis of that trapped compound over tens of minutes in the mass spectrometer 60.

In a specific embodiment, all gas flow lines mentioned above are 0.25 mm OD silica capillary tubing, and all connections between these lines and the valves or other components are with compression fittings using Vespel™ or Siltite™ ferules.

In FIG. 2, it will be noted that the first multi-port switching valve 110 is configured to couple its first input 111 to its second output 114 and to couple its second input 112 to its first output 113. The second multi-port switching valve 120 is configured to couple its first input 121 to its first output 123 and to couple its second input 122 to its second output 124. The effect of this is for effluent from the GC column 30 to be provided directly to the mass spectrometer 60 without passing through the peak broadener 50. The peak broadener 50 is instead supplied with helium from source 70 through to the waste line 80. This mode is used in an initial analysis step to determine a retention time and peak width for compounds of interest eluted from the GC column 30.

Figure 3:
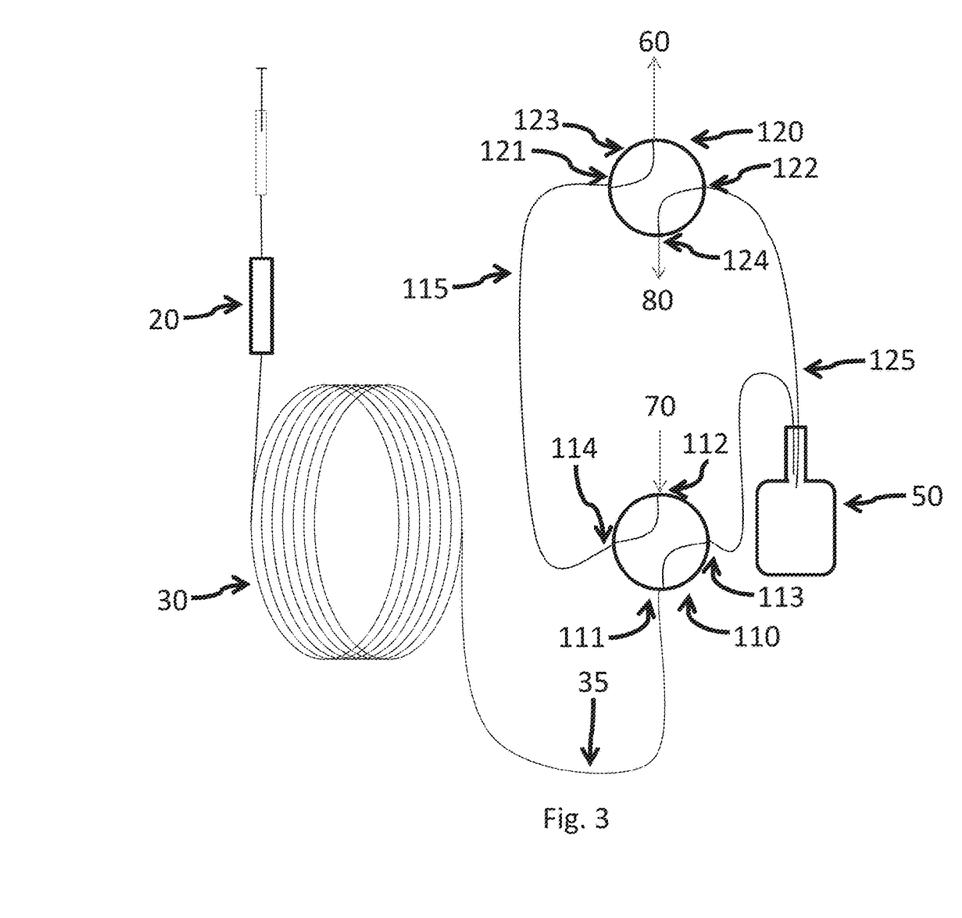
FIG. 3 illustrates the embodiment shown in FIG. 2, in a second configuration.

Referring next to FIG. 3, there is illustrated the embodiment shown in FIG. 2, in a second configuration. Here, the first multi-port switching valve 110 is configured to couple its first input 111 to its first output 113 and to couple its second input 112 to its second output 114. The second multi-port switching valve 120 is configured to couple its first input 121 to its first output 123 and to couple its second input 122 to its second output 124. In this mode, effluent from the GC column 30 is captured in the peak broadener 50 and no sample is provided to the mass spectrometer 80. This mode is used when a compound (peak) of interest is eluted from the GC column 30 and peak broadening is desirable. The timing for this is selected based on the retention time and peak width determined in the initial analysis step.

Figure 4:
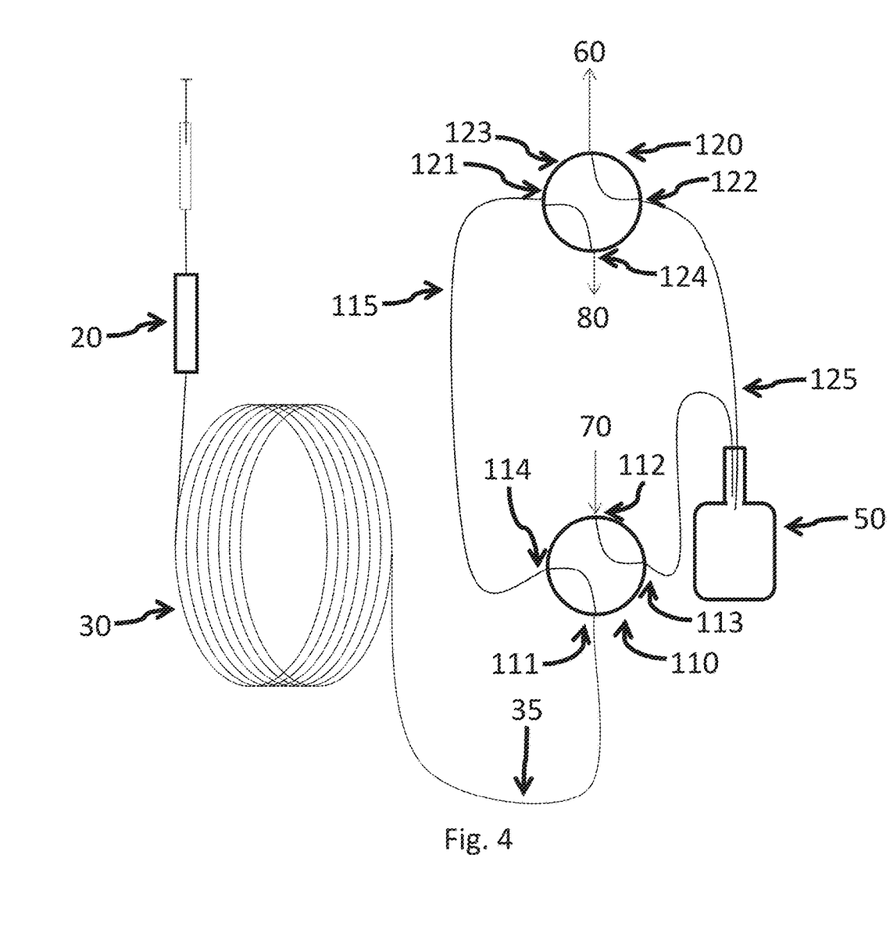
FIG. 4 illustrates the embodiment shown in FIG. 2, in a third configuration.

Referring next to FIG. 4, there is illustrated the embodiment shown in FIG. 2, in a third configuration. In this case, the first multi-port switching valve 110 is configured to couple its first input 111 to its second output 114 and to couple its second input 112 to its first output 113. The second multi-port switching valve 120 is configured to couple its first input 121 to its second output 124 and to couple its second input 122 to its first output 123. Thus, if the peak broadener 50 traps effluent from the GC column 30 in its reservoir volume, this is now transferred to the mass spectrometer 60 for analysis. The effluent from the GC column 30 is simply sent to the vacuum pumped waste line. Helium buffer gas is provided as a solvent blanking to the peak broadener 50, to protect the ion source.

Although not shown in any drawing, a fourth configuration can be conceived. There, the first multi-port switching valve 110 is configured to couple its first input 111 to its first output 113 and to couple its second input 112 to its second output 114. The second multi-port switching valve 120 is configured to couple its first input 121 to its second output 124 and to couple its second input 122 to its first output 123. This mode provides the effluent from the GC column 30 to the mass spectrometer 60 via the peak broadener 50. This mode operates similarly to one mode of operation of the existing IRMS system shown in FIG. 1. Such operation can be used when the time separation between peaks eluted from the GC column 30 is large.

In one method operation, the configuration shown in FIG. 2 may be used. Then, the effluent from the GC column 30 passes through the bypass line 115 directly into the mass spectrometer 60. When compounds that are not desirable for introduction to the ion source of the mass spectrometer 60 are eluting from the GC column 30, the second valve 120 can be rotated to the configuration of FIG. 4, to send the analyte stream to the waste line 80.

In another method of operation, a compound eluted from the GC column 30 may be analyzed and trapped in the peak broadener 50. The analyte introduction apparatus is plumbed according to the configuration described above and the sample is injected into the injection port of the GC column 30 using a gas or liquid syringe (injector 20), as appropriate. Second valve 120 is rotated to the configuration of FIG. 4, to send the analyte gas streams to the waste line when the solvent or any undesired peaks elute from the column.

The second valve 120 may then be rotated to the configuration of FIG. 2 to send analyte effluent to the ion source of the mass spectrometer 60 during periods when peaks of possible interest elute from the column (including those peaks one wishes to observe to precisely gauge the timing of elution of a peak of interest). Thus, this configuration may be used, for example, for recording a mass spectrum of at least a part of the effluent from the GC column, when a high precision and accuracy isotope ratio measurement is not desired. In this approach, the first valve 110 may initially be rotated to bypass the peak broadener volume (in accordance with the configuration of FIG. 2 or FIG. 4), sending all eluting peaks to the second valve 120 (and then to the waste line 80 or the mass spectrometer 60, depending on the position of the second valve 120).

Immediately before elution of a compound of interest, the first valve 110 is rotated in line with the configuration of FIG. 3, to send that peak towards the volume of the peak broadener 50. The first valve 110 should be returned to the position as shown in FIG. 2 as soon as the peak of interest has fully eluted from the column to prevent contamination of the peak broadener 50 volume with later-eluting compounds. Once the compound of interest is trapped in the peak broadener 50, the second valve 120 can be switched to the configuration of FIG. 4, to permit the gas exiting the peak broadener 50 to move toward the ion source of mass spectrometer 60, while any later eluting peaks are sent to the waste line 80.

This technique allows accurate cut-out of GC peaks from chromatograms into the peak broadener. Improved precision and accuracy in corresponding isotope ratio analysis are thereby attained.

In general terms, there is provided a method of isotope ratio mass spectrometry, comprising: injecting a sample for analysis into a gas chromatography column; directing an effluent from the gas chromatography column to a switching arrangement; and selecting a configuration of the switching arrangement. In another aspect, there is provided an isotope ratio mass spectrometry system, comprising: a gas chromatography column, configured to receive a sample for analysis by injection; and a switching arrangement, arranged to receive an effluent from the gas chromatography column. The switching arrangement has a selectable configuration. This improves the precision and accuracy of GC isotope ratio measurements on mass spectrometers by increasing the fraction of analyte ions delivered to the mass analyzer for analysis. Features applicable to either aspect are now described.

In either aspect, the switching arrangement is configured to have multiple operating modes. In a first mode, the effluent from the gas chromatography column is provided as an input to a peak broadener. In a second mode, an effluent from the peak broadener is provided to a mass spectrometer for isotope ratio mass spectrometry without the effluent from the gas chromatography column being provided as an input to the peak broadener. Optionally, in the second mode, the effluent may be provided from the gas chromatography column to a waste line for disposal and/or a buffer (or blanking) gas may be provided as an input to the peak broadener. In a third mode, the effluent from the gas chromatography column is provided to the mass spectrometer for isotope ratio mass spectrometry without passing through the peak broadener (in particular, directly). In a fourth mode, the effluent is provided from the gas chromatography column to the mass spectrometer for isotope ratio mass spectrometry via the peak broadener. The switching arrangement may be configured to be switchable between any two or more of the above modes. Preferably, the switching arrangement is configured to be switchable at least between the first and second modes.

The first mode is advantageously selected when the effluent from the gas chromatography column comprises a compound of interest. A compound of interest may be a compound on which it is desired to perform an isotope ratio measurement at high precision and accuracy, such that the peak broadener is employed to broaden the peak of the compound and permit longer measurement times in the mass analyzer. The isotope ratio precision generally scales with the inverse of the square root of the number of mass spectra recorded (approximately the measurement time), such that longer measurement times provide more precise results. Additionally or alternatively, the second mode may be selected when the effluent from the gas chromatography column does not comprise a compound of interest. Optionally, the third or fourth mode is selected when the effluent from the gas chromatography column comprises a compound of interest, or simply a compound or compounds for which a mass spectrum is desired. In the preferred embodiment, the third mode is selected in an initial analysis step. This may be used to determine a retention time and/or peak width for the compound of interest. The selection of the first mode may then be performed in a subsequent analysis step (that is, subsequent to the initial analysis step and preferably in a subsequent scan) is based on the determined retention time and/or peak width. More preferably, the timing of the selection of the first mode is determined in this way.

In the preferred embodiment, the peak broadener comprises a reservoir volume through which gas flows. The reservoir volume may be provided by a tube or flask. The volume dimensions of the reservoir volume may be determined based on a total time of analysis required to achieve a desired isotope ratio precision.

Preferably, the switching arrangement comprises a plurality of switching devices. Each switching device beneficially has first and second inputs and first and second outputs. In a first arrangement of each switching device, the first input is coupled to the first output and the second input is coupled to the second output and in a second arrangement, the first input is coupled to the second output and the second input is coupled to the first output. In embodiments, the first switching device is configured to receive an effluent from the gas chromatography column as its first input and a buffer gas source as its second input, its first output being coupled to the input of the peak broadener. Beneficially, the second switching device is coupled to the second output of the first switching device as its first input and an output of the peak broadener is provided as its second input, its first output being coupled to a sample input of the mass spectrometer and its second output being coupled to a waste line.

Figure 5:
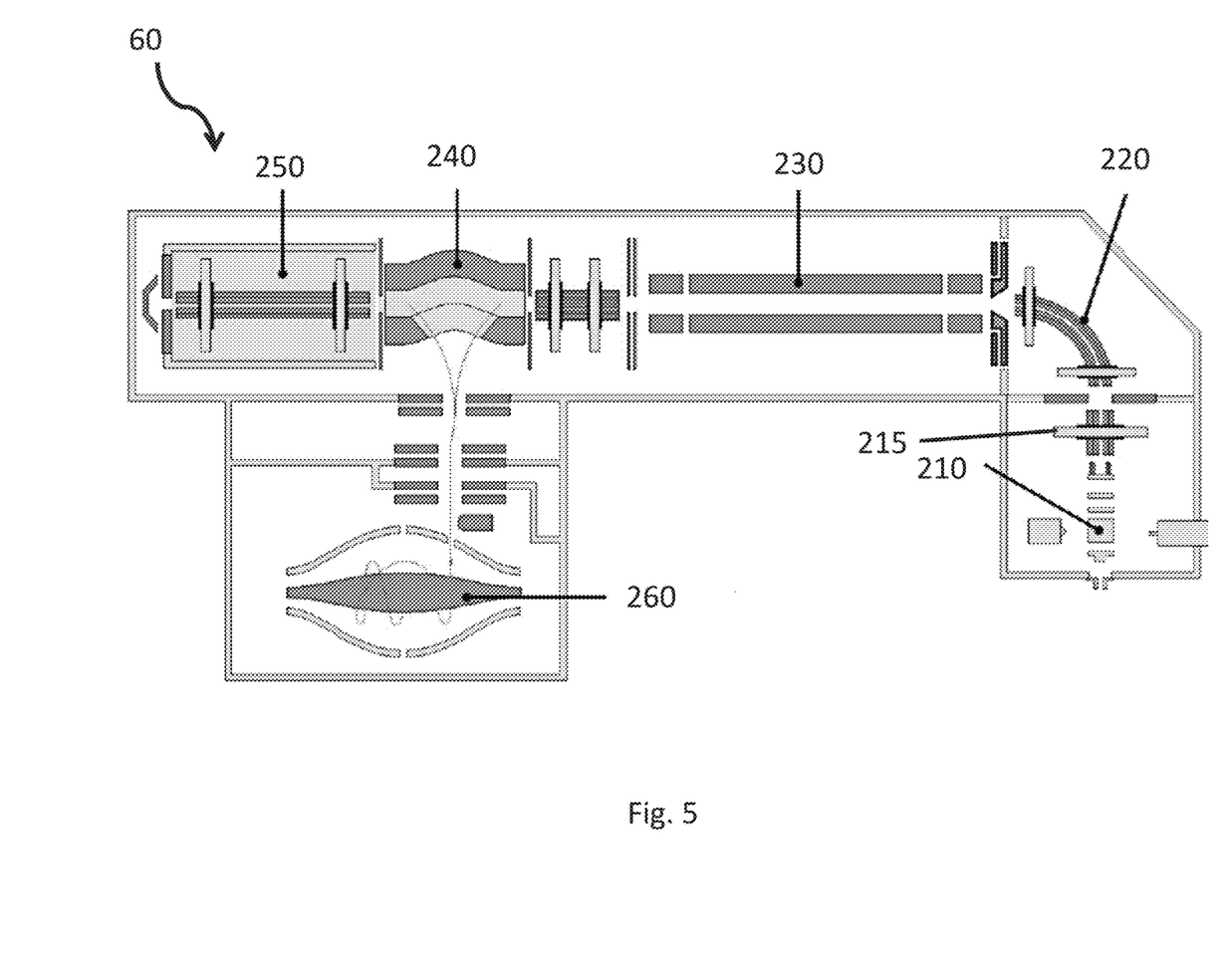
FIG. 5 shows a schematic of an example mass spectrometer for use with the embodiment of FIG. 2.

With reference to FIG. 5, there is shown a schematic of an example mass spectrometer for use with the embodiment of FIGS. 2 to 4. The mass spectrometer 60 comprises: an ion source 210 (specifically using electron ionization, electrospray ionization or chemical ionization); an RF lens 215; an ion guide 220 (in the form of a bent flatapole ion optical device with an axial field); a quadrupole mass filter 230; a curved ion trap (C-trap) 240; a Higher-energy Collisional Dissociation (HCD) cell 250; and an orbital trapping mass analyzer 260. In the mass spectrometer 60, the ion source 210 generates ions that enter the RF lens 215 before being guided by the ion beam guide ion optics 220 to the quadrupole mass filter 230. The ions may be collisionally cooled at this stage. A mass isolation window (for example, ≥0.4 amu range, with resolution of ~1000) can be set by the mass filter 230 to transmit ions of the desired mass to a downstream ion trap (C-Trap) 240, where ions can be accumulated before ejection of the ions to the orbital trapping mass analyzer 260 for mass analysis. If required, the ions can be transmitted through the C-trap 240 to the downstream HCD cell 250 where ions can be collisionally cooled and/or fragmented before being returned to the C-trap 240 and subsequently mass analyzed in the orbital trapping mass analyser 260. These steps can be repeated as desired.

This mass spectrometer 60 is a hybrid quadrupole-orbital trapping mass spectrometer marketed under the name Q Exactive™ GC Hybrid Quadrupole-Orbitrap™ by Thermo Fisher Scientific, Inc., the details of which are incorporated by reference. Instrument control and primary data processing (that is, conversion of orbital trapping mass analyzer transients into a mass spectrum with associated intensities) are performed using the Tune™ and Xcalibur™ software packages provided by Thermo Fisher Scientific, Inc. Details of the IRMS method will now be discussed. Further details can be found in our co-pending patent application, GB1701986.0, the details of which are incorporated by reference.

The mass spectrometer typically analyses the eluate over time, for example at set sampling intervals, to provide a mass chromatogram, that is a series of mass spectra measured at a series of data points across retention time. At a point during the sample elution, the mass spectrometer records the mass spectrum of the peak of interest from the GC column 30 corresponding to at least the molecular species having an isotope ratio to be determined. The mass spectrometer records the mass spectrum of the eluate as it emerges from the GC column 30 in a sequence of data acquisition cycles taken over time. The mass spectrum is typically recorded across the range of retention times from 0 minutes (or sample injection) until at least the mass spectrum of the molecular species having an isotope ratio to be determined has been recorded across its elution peak. As described, the switching arrangement (of first valve 110 and second valve 120) is configured during the period of the elution peak of interest to send some eluate to the peak broadener 50 and thereby increase the peak width (or elution time, that is the time it spends in the eluate) for the molecular species having an isotope ratio to be determined. Thus, the total mass analysis time for the molecular species having an isotope ratio to be determined is extended by the peak broadener 50, that is by increasing the number of measurement points by a factor of the ratio of the peak widths (peak width with flow reduction/peak width without flow reduction). Preferably, the isotope ratio precision is <20 δ‰, preferably (in order of increasing preference) <15δ‰, or <10δ‰, or <7δ‰, or <5δ‰, or <3δ‰, or <1δ‰, or <0.5δ‰, or <0.1δ‰.

The mass spectrum recorded includes an isotopic pattern from which it is possible to resolve a plurality of isotopic peaks, that is peaks due to different isotopologues of the molecular species having an isotope ratio to be determined. From analysis of the isotopically resolved mass spectrum, an isotope ratio can be determined. For example, from intensities of two or more resolved isotopic peaks in the mass spectrum, often where one is the monoisotopic peak, it is possible to determine an isotope ratio (optionally expressed as a delta (δ) value) for an element. Preferred elements of interest to determine an isotopic ratio for are C, N, O, H, S, P, Cl, Br and Si. Some common isotope ratios to be determined include $^{13}C/^{12}C$, $^{14}C/^{12}C$, $^{16}N/^{14}N$, $^{2}H/^{1}H$, $^{18}O/^{16}O$, $^{17}O/^{16}O$ or $^{34}S/^{32}Cl$, $^{37}Cl/^{35}Cl$, $^{81}Br/^{79}Br$, $^{29}Si/^{28}Si$, $^{30}Si/^{28}Si$, etc.

The isotope ratio determination can be based on the intensities, for example on comparing (that is finding the ratio of) the intensities, of mass peaks of isotopologues of the molecular species, in which the isotopologues have different nominal mass (typically differing by one or two nominal mass units). Typically, the monoisotopic peak (for the monoisotopic isotopologue) in the mass spectrum of the at least one molecular species having an isotope ratio to be determined, for example the [M+H]$^+$ peak in a mass spectrum obtained from an electrospray source, can provide an isotope abundance for the particular light isotope of interest (for instance $^{12}C$, $^{14}N$, $^{16}O$, $^{1}H$, $^{32}S$) and an A+1 peak or A+2 peak (where A is the monoisotopic mass peak) for an A+1 isotopologue or A+2 isotopologue can provide an isotope abundance for the particular heavy isotope of interest (for example $^{13}C$, $^{16}N$, $^{18}O$, $^{2}H$, $^{34}S$).

The isotope ratio determination may thus comprise comparing the intensity of a monoisotopic mass peak A with an A+1 mass peak or A+2 mass peak to provide an isotope ratio of a light isotope and a heavy isotope of interest. The high resolving power of the mass spectrometer, especially a spectrometer comprising an orbital trapping mass analyzer 260, has been found able to resolve a particular A+1 peak (or A+2 peak) of an isotopologue having the particular heavy isotope of interest ($^{13}C$, or $^{15}N$, or $^{18}O$, or $^{2}H$, or $^{34}S$ etc.), that is resolve that particular isotopologue peak from other A+1 nominal mass peaks (or A+2 nominal mass peaks) of isotopologues having another heavy isotope. Where appropriate, isotope ratio determination can also include an analysis based on one or more higher mass peaks, such as an A+3 peak, an A+4 peak and so on.

Each isotopologue mass peak used for the isotope ratio determination should preferably be resolved from at least any other mass peaks at the same nominal mass which are more than 20%, or more preferably more than 10%, or most preferably more than 5%, of the intensity of the isotopologue mass peak. For example in an embodiment, the resolved isotope peak pattern of A+1 peaks shows that a $^{13}C$ isotopologue peak can be sufficiently resolved from a $^{15}N$ isotopologue peak or $^{2}H$ peak. Further, the resolved isotope peak pattern of A+2 peaks shows that an $^{18}O$ isotopologue peak can be sufficiently resolved from a $^{13}C_2$ isotopologue peak or a $^{13}C^{15}N$ isotopologue peak. Thus, the disclosure may enable analysis of multiply substituted isotopologues as well as singly substituted isotopologues. The mass analysis therefore preferably resolves the monoisotopic peak from A+1 and A+2 peaks. The mass analysis further preferably resolves two or more A+1 isotopologues and/or two or more A+2 isotopologues from each other.

In some embodiments, the isotope ratio determination can be based on the intensities, for example on comparing (that is, finding the ratio of) the intensities, of mass peaks of isotopologues of the molecular species, in which the isotopologues have the same nominal mass. For example, the isotope ratio determination can be based on a ratio of the $^{15}N$ isotopologue peak to the $^{13}C$ isotopologue peak.

The mass analysis is preferably performed with a sufficient resolving power (R) to resolve mass peaks of isotopologues of the at least one molecular species, for example to resolve the two most abundant mass peaks at the nominal mass of at least one of the isotopologues used to determine the isotope ratio (preferably at the nominal masses of each of the isotopologues used to determine the isotope ratio). The two most abundant mass peaks that are resolved at the same nominal mass are typically two isotopologues. The two most abundant mass peaks at the nominal mass are preferably peaks that if not resolved would each contribute significantly to the isotope ratio to be determined (for instance by contributing >20%, or >10%, or >5% of the peak intensity of the isotopologue at the nominal mass). The mass analysis is preferably performed with a mass resolving power high enough to resolve the two most abundant A+1 isotopologues and/or the two most abundant A+2 isotopologues (where A is the monoisotopic mass peak).

Referring to the general description used above, further features may now be defined. In some embodiments, the mass spectrometer has a detection time that is longer than an ion storage time and preferably significantly longer (for instance, 2, 3, 5, 10, 20, 50, 100, 500 or 1000 times longer). For instance, the detection time may be about or at least 250 ms, 500 ms, 750 ms, or 1s. In preferred embodiments, the mass spectrometer is able to analyze in one acquisition cycle the full mass spectrum of each of the components eluting from the GC column, that is all mass (m/z) peaks of a compound can be recorded in a single acquisition cycle. Spectrometers that comprise high resolution and accurate mass (HR-AM) analyzers are preferred. Preferred spectrometers include mass analyzers of the following types: a Fourier Transform Mass Spectrometry (FTMS) mass analyzer; electrostatic traps such as orbital trapping analyzer which are typically FTMS; FT-ICR mass analyzers; and single or multi-reflection TOF mass analyzers. In such analyzers, all mass (m/z) peaks of a compound are measured during one acquisition cycle (herein referred to as measurement 'in parallel'), that is from a single injection of ions into the analyzer. The method may further comprise analyzing effluent from the switching arrangement in the mass spectrometer. For example, the method may comprise generating ions in an ion source of the mass spectrometer from effluent received from the switching arrangement. Conversely, the mass spectrometer may comprise an ion source, configured to receive effluent from the switching arrangement and generate ions for analysis from the received effluent. Optionally, the method may further comprise storing generated ions (or ions derived from the generated ions) in an ion storage device of the mass spectrometer. In the same way, the mass spectrometer may comprise an ion storage device, arranged to receive ions generated by the ion source and store the received ions. The ions stored may be ejected to a mass analyzer of the mass spectrometer for a mass analysis.

Exemplary analytical procedures using the IRMS system 100 of FIG. 2 and mass spectrometer of FIG. 5 will now be described. For this purpose, it can be understood that the smallest organizing unit of an analysis is the 'scan'. A scan may be defined by four features:

(1) a mass window admitted through quadrupole mass filter 230 (for example when a hybrid quadrupole-orbital trapping mass spectrometer is used, as discussed above) and stored in the C-trap 240 before being passed to the orbital trapping mass analyzer 260;

(2) a mass window of mass analysis, which could be wider than a former window, especially for MS/MS experiments;

(3) a total ion charge in that mass window that is stored in the C-trap 240 prior to analysis (this charge is controlled by varying an Automatic Gain Control, AGC, target); and (4) a period of observation of the trapped ion population (that is, the duration over which a transient is observed prior to ejecting ions from the trap and performing a FFT on the observed signal of trap voltage against time; this period of observation of the transient may have an important effect on the mass resolution achieved at each point in the mass spectrum).

A second unit used to define an analysis is the 'cycle'. A cycle comprises one or more scans performed in series. When a cycle contains more than one scan, the transients recorded by those scans are signal averaged prior to performing the FFT, increasing the overall signal to noise ratios of reported peaks. The word 'analysis' can then refer to the set of cycles over which a given sample was measured.

Figure 6A:
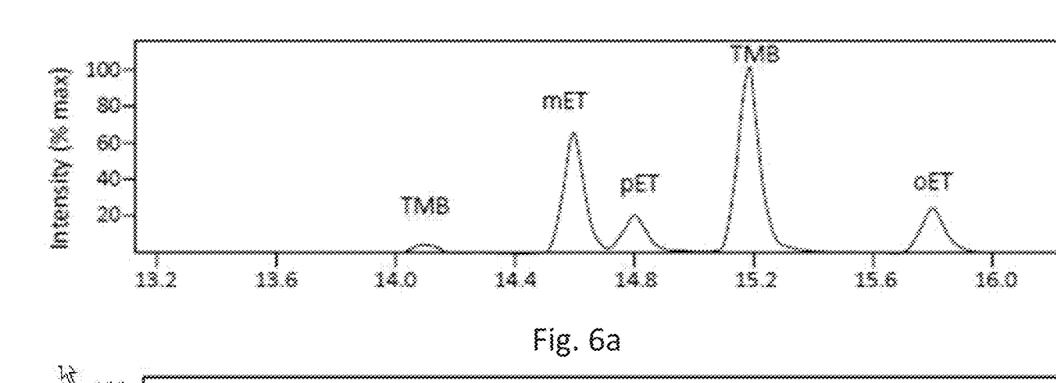
FIG. 6a plots time varying ion signals observed when introducing analyte to the ion source of an isotope ratio mass spectrometry system in accordance with the embodiment of FIG. 2.

Results and observations using a system in accordance with that shown in FIGS. 2 to 5 are now discussed. Referring next to FIG. 6a, there are plotted time-varying ion signals observed when introducing analyte to the ion source of an isotope ratio mass spectrometry system in accordance with the embodiment of FIG. 2. In particular, this shows an example total ion chromatogram of fragment ion, $C_8H_9^+$ measured in the mass range 100-125 amu for several compounds (trimethyl benzenes, TMB, and para, meta or ortho ethyl toluene, p. m or o-ET) eluted from the GC column 30 after injection of a natural condensate. Direct elution of gas or liquid from the GC column 30 was used, in accordance with the mode shown specifically in FIG. 2.

Figure 6B:
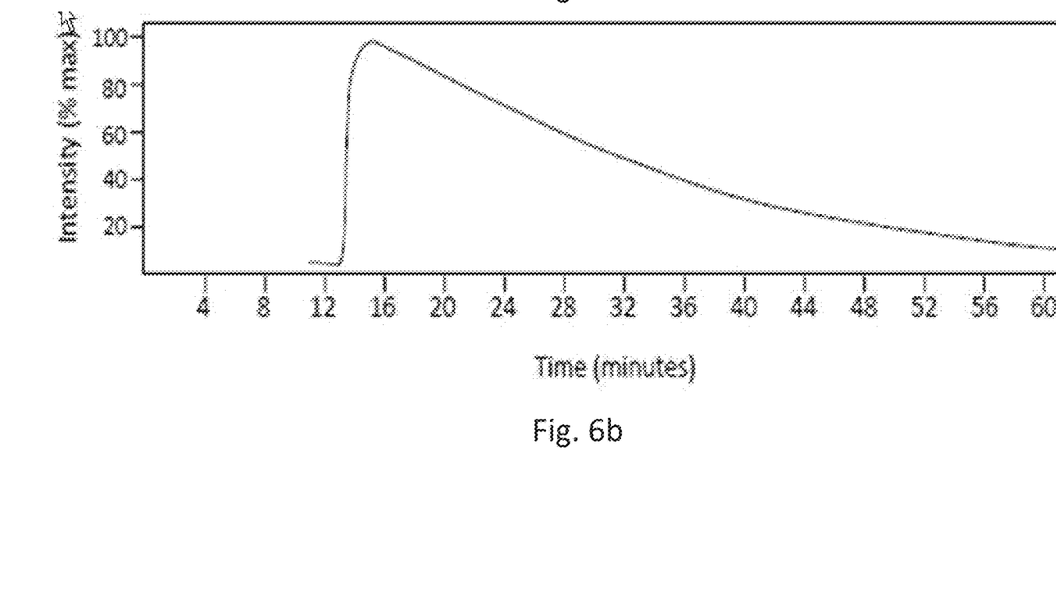
FIG. 6b plots a total ion current measured in a specific mass range for meta-ethyl toluene captured by a peak broadener of an isotope ratio mass spectrometry system in accordance with the embodiment of FIG. 3.

Next with reference to FIG. 6b, there is plotted a total ion current measured for the m-ethyl toluene fragment ion, $C_8H_9^+$, after its compound peak was captured by a peak broadener 50 of an IRMS system in accordance with the embodiment of FIG. 3. The time variation is over an approximately one hour period after its peak was trapped in a 20 cc reservoir of peak broadener 50 and allowed to slowly purge into the ion source 210.

Figure 7:
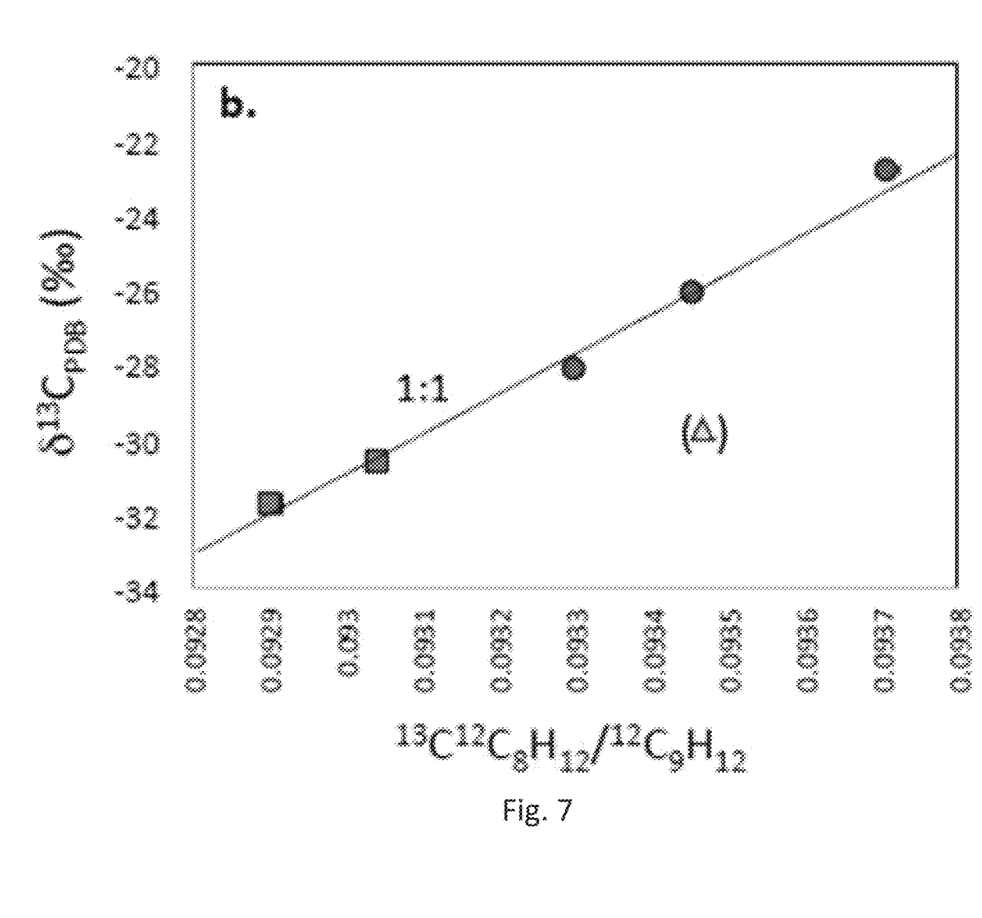
FIG. 7 depicts experimentally measured carbon isotope ratios of full molecular ions of six ethyl toluenes, using an isotope ratio mass spectrometry system in accordance with the embodiment of FIGS. 2 to 5.

Referring to FIG. 7, there are depicted experimentally measured (raw) carbon isotope ($^{13}O/^{12}O$) ratios of full molecular ions of six ethyl toluenes, using an IRMS system in accordance with the embodiment of FIGS. 2 to 5. The six ethyl toluenes represent three isomers, compared to their independently known $\delta^{13}C$ Pee Dee Belemnite (PDB) values. The line is 1:1 proportionality. All measurements were made by the peak broadener method, and include both simple reference standard solutions and peaks captured from complex, multi-component samples.

In particular, FIG. 7 illustrates representative data documenting experimental reproducibility across multiple analyses, including long-time-scale observations of sample-standard differences for GC peaks analyzed with the peak broadener 50. The data point marked with a ( ) bracket represents the average of a set of measurements that failed to reproduce within 2× shot noise limits. For each set of data, experimental errors found are generally similar to expected shot noise limits to precision for the conditions and durations of the measurements in question (which are always less than 1‰). The general finding is that experimental reproducibility is comparable to shot-noise limits in precision across a range of experimental methods, analytes and time scales.

The external errors for isotope ratios measured on directly eluted peaks are generally shot-noise limited, where the shot noise is primarily controlled by the duration of the peak and the setting of the AGC control (that is, time multiplied by intensity). The mass resolution of the analysis has a secondary effect. Representative findings are that a given peak will elute over a period of approximately 10 seconds; at an AGC setting of $2\times10^5$, approximately 55,000 ions per second are collected for the unsubstituted molecular ion peak and approximately 5,000 ions per second for the singly 13C substituted peak. The shot noise limit on the $^{13}O/^{12}O$ ratio measured for this peak for the 10-second integral of its duration is typically 4.7‰ (1 se). This is approximately a factor of 10 worse than the error achieved for analyses of peaks that are trapped in the peak broadener 50 and analyzed over periods of tens of minutes.

It will therefore be appreciated that variations to the foregoing embodiments of the inventive concepts can be made while still falling within the scope of the inventive concepts. Each feature disclosed in this specification, unless stated otherwise, may be replaced by alternative features serving the same, equivalent or similar purpose. Thus, unless stated otherwise, each feature disclosed is one example only of a generic series of equivalent or similar features. Specific variations will now be discussed.

The disclosure is largely focused on the use of an orbital trapping mass analyzer for isotope ratio mass spectrometry. It be understood that other types of mass analyzer can be considered, especially those based on electrostatic traps, in particular using FTMS. Additionally or alternatively, the type of GC system used may be varied from that described herein. Types of buffer or blanking gas other than helium may be employed and/or the waste line may be implemented differently from that described above. The switching arrangement may also differ from that disclosed herein, for instance in the way that the multi-port valves are coupled and/or in the type of switches used. A specific alternative example will now be briefly discussed.

Figure 8:
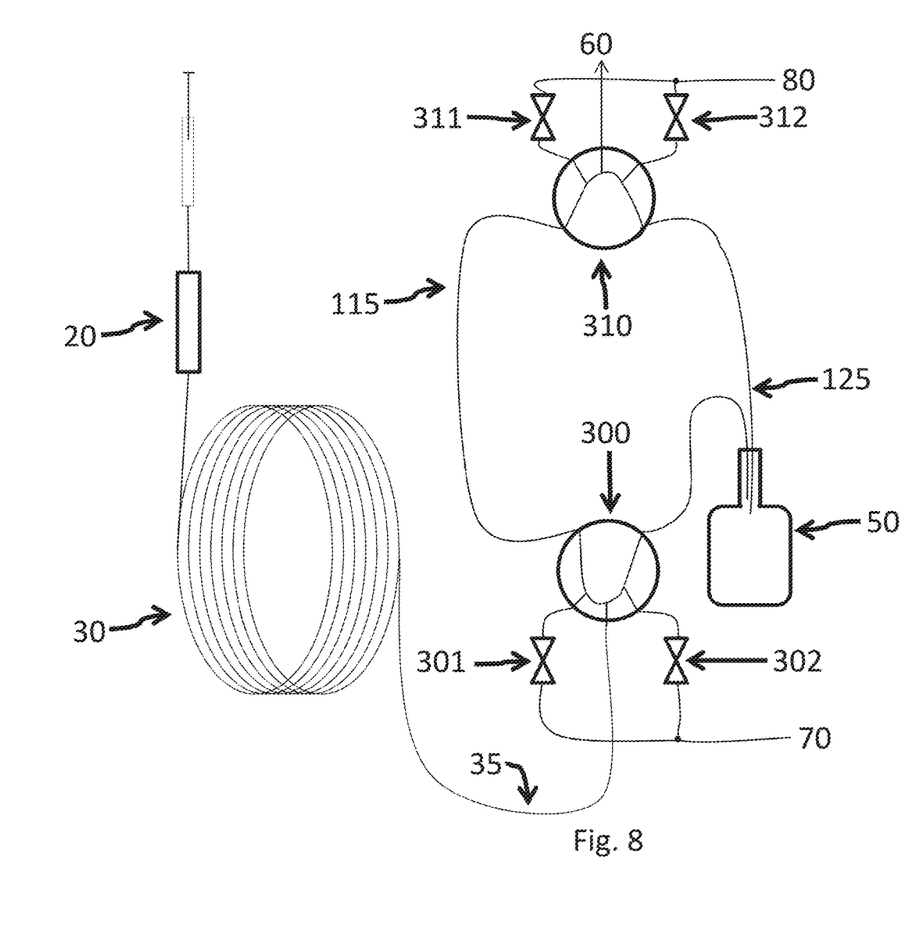
FIG. 8 shows a schematic of an isotope ratio mass spectrometry system in accordance with a second embodiment of the disclosure, using Deans' switches.

With reference to FIG. 8, there is shown a schematic of an IRMS system in accordance with a second embodiment of the disclosure, using Deans' switches. A Deans' switch can be used to switch one inlet to one of two outlets, by means of two auxiliary flows. Such devices are described in "Comprehensive Theory of the Deans" Switch As a Variable Flow Splitter: Fluid Mechanics, Mass Balance, and System Behavior", Boeker et al, Anal. Chem., 2013, 85 (19), pp 9021-9030, the details of which are hereby incorporated by reference. Where the same features are indicated as shown in FIGS. 1 to 4, identical reference numerals have been used. In this embodiment, the multi-port switching valve 110 of FIGS. 2 to 4 is replaced by a first Deans' switch comprising: a first Deans' Module 300; first valve 301; and second valve 302. The multi-port switching valve 120 of FIGS. 2 to 4 is replaced by a second Deans' switch comprising: Deans' Module 310; third valve 311; and fourth valve 312.

The operation of the embodiment of FIG. 8 is similar to that of the embodiment shown in FIGS. 2 to 4. To effect the mode of operation shown in FIG. 2, the first valve 301 is closed, the second valve 302 is open, the third valve 311 is closed and the fourth valve 312 is open. To effect the mode of operation shown in FIG. 3, the first valve 301 is open, the second valve 302 is closed, the third valve 311 is open and the fourth valve 312 is closed. To effect the mode of operation shown in FIG. 4, the first valve 301 is closed, the second valve 302 is open, the third valve 311 is open and the fourth valve 312 is closed.

In the generalized description previously detailed, it may be understood that the plurality of switching devices may each comprise a multi-port switching valve or a Deans' switch configuration. Other valve types could be used alternatively.

A range of further other possible implementations may be considered. Some of these need not be used in conjunction with the configuration of FIGS. 2 to 4 and may be used with the configuration of FIG. 1 or other types of IRMS system. For example, a means for stabilizing the partial pressure of the compound of interest eluting from the peak broadening device could be provided. Such a means might include one or more of: an adjustable volume reservoir, such as a bellows device, or a balloon filled with gas inside the peak broadener flask; compensating the partial pressure loss by filling part of the reservoir with a liquid and/or increasing gas flow into the reservoir volume; and increasing the GC oven (or reservoir) temperature to expand the gas inside the peak broadener and increase the total pressure inside the device, resulting in improved partial pressure stability. Adjusting the internal volume of the peak broadener may allow improved precision and accuracy in isotope ratio analysis. Deactivation coatings may be used for the peak broadener, to avoid fractionation by adsorption to the walls (for instance, siliylation) of the glass surface. For example, dimethyldichlorosilane could be used to coat regular glass or silica or quartz with a silyl coating. Examples of such derivatization reagents are produced by Sigma-Aldrich Co. and further information can be found, for instance in "Deactivation of glass capillary columns by silylation. Part 1: Principles and basic technique", K. Grob, et al, Journal of Separation Science, volume 2, issue 1, January 1979, pages 31-35. Alternatively, glass-like microcoatings could be provided on metal reservoirs used as peak broadening devices. Commercial glass-like microcoatings on steel parts are for example: Sulfinert™, Siltek™, Silcosteel™, SilcoNert™ 2000, or SilcoNert™ 1000 coatings produced by SilcoTek™ Corporation.

Instead of using a defined volume (flask, bellow) to trap the compound of interest, a low temperature trap may be provided. This may allow controlled thermal desorption or directed gas flows to desorb the substances in a second step. Temperature or gas flow control may be applied to adjust the desorption rate and keep the analyte partial pressure constant in the ion source.

Although the use of a single peak broadener 50 has been considered, multiple peak broadeners may be used. For instance, this may allow capture and analysis of more than one analyte from a complex chromatogram. Also, more than two switching devices may be provided, for additional control of paths, especially when using more than one mass spectrometer and/or more than one peak broadener.

In terms of the general description, a range of additional features may be considered. For example, the method may further comprise stabilizing a partial pressure of the effluent from the peak broadener. Optionally, stabilizing a partial pressure comprises one of: adjusting a volume of the peak broadener (using a bellows device and/or gas-filled balloon within the peak broadener); compensating for a partial pressure loss by filling part (not all) of the reservoir volume with a liquid and/or increasing gas flow into the reservoir volume; and increasing a temperature of the reservoir volume to expand gas in the peak broadener and/or increasing the total pressure inside the peak broadener.

The peak broadener may have walls (or more specifically, its reservoir volume may be defined by walls) with a coating on the internal surface. Using a peak broadener with coated internal surfaces may avoid artifacts of isotopic fractionation caused by adsorption of analytes to the walls of the device. The coating may be a deactivation coating. Additionally or alternatively, the reservoir volume of the peak broadener has at least part defined by a metal surface coated with a glass-like microcoating. In some embodiments, the peak broadener comprises: a gas trap configured to receive the input to the peak broadener; and a controlled desorption stage, configured to desorb effluent received from the gas trap. Then, the method may further comprise setting a rate of desorption for the controlled desorption stage to effect a desired and/or constant partial pressure of effluent from the peak broadener. Setting a rate of desorption optionally comprises one of: setting or controlling a temperature for the controlled desorption stage, the controlled desorption stage comprising a thermal desorption arrangement; and controlling a gas flow for the controlled desorption stage, the controlled desorption stage comprising a directed gas flow desorption arrangement.

More than one or even more than two peak broadeners may be used. In some such embodiments, the peak broadener is a first peak broadener. Then, a fifth mode of the switching arrangement may be considered, in which the effluent from the gas chromatography column is provided to a second peak broadener. Moreover, in a sixth mode of the switching arrangement, an effluent from the second peak broadener is provided to the mass spectrometer for IRMS without the effluent from the gas chromatography column being provided as an input to the second peak broadener. In this sixth mode, the effluent from the gas chromatography column is optionally provided as an input to the first peak broadener. A third peak broadener may be provided (or indeed, more than three peak broadener may be provided). Then for example, in a seventh mode, the effluent from the gas chromatography column is provided to the third peak broadener. In an eighth mode, an effluent from the third peak broadener is provided to the mass spectrometer for isotope ratio mass spectrometry without the effluent from the gas chromatography column being provided as an input to the third peak broadener. Advantageously, the effluent from the third peak broadener is provided to the mass spectrometer for isotope ratio mass spectrometry after the effluents from the first and second peak broadeners are provided to the mass spectrometer for isotope ratio mass spectrometry. In this way, three or more peak broadeners may capture three or more compounds, which may then be analyzed one after the other (sequentially).

The effluent from the first peak broadener is advantageously provided to the mass spectrometer for isotope ratio mass spectrometry initially, the effluent from the second peak broadener being provided to the mass spectrometer for isotope ratio mass spectrometry subsequently. Additional embodiments, in which one or more further peak broadeners are added to the configuration may be considered. Corresponding modes for providing effluent from the gas chromatography column is provided to one or more of the further peak broadeners and/or providing an effluent from each peak broadener to the mass spectrometer for IRMS (without effluent from the gas chromatography column being provided as an input to the peak broadener) may be provided. In these cases; the effluent from the each peak broadener may be sequentially be provided to the mass spectrometer for isotope ratio mass spectrometry.

As used herein, including in the claims, unless the context indicates otherwise, singular forms of the terms herein are to be construed as including the plural form and vice versa. For instance, unless the context indicates otherwise, a singular reference herein including in the claims, such as "a" or "an" (such as a sample) means "one or more" (for instance, one or more samples). Throughout the description and claims of this disclosure, the words "comprise", "including", "having" and "contain" and variations of the words, for example "comprising" and "comprises" or similar, mean "including but not limited to", and are not intended to (and do not) exclude other components.

The use of any and all examples, or exemplary language ("for instance", "such as", "for example" and like language) provided herein, is intended merely to better illustrate the inventive concepts and does not indicate a limitation on the scope of the inventive concepts unless otherwise claimed. No language in the specification should be construed as indicating any non-claimed element as essential to the practice of the inventive concepts.

Any steps described in this specification may be performed in any order or simultaneously unless stated or the context requires otherwise.

All of the features disclosed in this specification may be combined in any combination, except combinations where at least some of such features and/or steps are mutually exclusive. In particular, the preferred features of the inventive concepts are applicable to all aspects of the inventive concepts and may be used in any combination. Likewise, features described in non-essential combinations may be used separately (not in combination).

The invention claimed is:

1. A method of isotope ratio mass spectrometry, comprising:
   injecting a sample for analysis into a gas chromatography column;
   directing an effluent from the gas chromatography column to a switching arrangement; and
   selecting a configuration of the switching arrangement, such that: in a first mode, the effluent from the gas chromatography column is provided as an input to a peak broadener; and in a second mode, an effluent from the peak broadener is provided to a mass spectrometer for isotope ratio mass spectrometry without the effluent from the gas chromatography column being provided as an input to the peak broadener.

2. The method of claim 1, wherein the step of selecting the configuration of the switching arrangement comprises selecting the first mode when the effluent from the gas chromatography column comprises a compound of interest and/or selecting the second mode when the effluent from the gas chromatography column does not comprise a compound of interest.

3. The method of claim 1, wherein the step of selecting the configuration of the switching arrangement comprises, in the second mode, providing the effluent from the gas chromatography column to a waste line for disposal and/or providing a buffer gas as a further input to the peak broadener.

4. The method of claim 1, wherein the step of selecting the configuration of the switching arrangement comprises, in a third mode, providing the effluent from the gas chromatography column to the mass spectrometer for isotope ratio mass spectrometry without passing through the peak broadener.

5. The method of claim 4, wherein the step of selecting the configuration of the switching arrangement comprises selecting the third mode when the effluent from the gas chromatography column comprises a compound of interest.

6. The method of claim 4, wherein the third mode is selected in an initial analysis step to determine a retention time and peak width, the selection of the first mode in a subsequent analysis step being based on the determined retention time and peak width.

7. The method of claim 1, wherein the step of selecting the configuration of the switching arrangement comprises, in a fourth mode, providing the effluent from the gas chromatography column to the mass spectrometer for isotope ratio mass spectrometry via the peak broadener.

8. The method of claim 1, wherein the mass spectrometer comprises an orbital-trapping type mass analyzer.

9. The method of claim 1, wherein the peak broadener comprises a reservoir volume through which gas flows.

10. The method of claim 9, further comprising:
    stabilizing a partial pressure of the effluent from the peak broadener.

11. The method of claim 10, wherein the step of stabilizing a partial pressure comprises one of:
    adjusting a volume of the peak broadener;
    compensating for a partial pressure loss by filling part of the reservoir volume with a liquid and/or increasing gas flow into the reservoir volume; and
    increasing a temperature of the reservoir volume to expand gas in the peak broadener and/or increasing a total pressure inside the peak broadener.

12. The method of claim 10, wherein the peak broadener has an internal surface provided with a deactivation coating and/or wherein the reservoir volume of the peak broadener has at least part defined by a metal surface coated with a glass-like microcoating.

13. The method of claim 1, wherein the peak broadener comprises: a gas trap configured to receive the input to the peak broadener; and a controlled desorption stage, configured to desorb effluent received from the gas trap, the method further comprising:
- setting a rate of desorption for the controlled desorption stage to effect a constant partial pressure of effluent from the peak broadener.

14. The method of claim 13, wherein the step of setting a rate of desorption comprises one of:
- controlling a temperature for the controlled desorption stage, the controlled desorption stage comprising a thermal desorption arrangement; and
- controlling a gas flow for the controlled desorption stage, the controlled desorption stage comprising a directed gas flow desorption arrangement.

15. The method of claim 1, wherein the peak broadener is a first peak broadener, the method further comprising:
- in a fifth mode, the effluent from the gas chromatography column is provided to a second peak broadener; and
- in a sixth mode, an effluent from the second peak broadener is provided to the mass spectrometer for isotope ratio mass spectrometry without the effluent from the gas chromatography column being provided as an input to the second peak broadener.

16. The method of claim 15, wherein the effluent from the first peak broadener is provided to the mass spectrometer for isotope ratio mass spectrometry initially and the effluent from the second peak broadener is provided to the mass spectrometer for isotope ratio mass spectrometry subsequently.

17. The method of claim 16, further comprising:
- in a seventh mode, the effluent from the gas chromatography column is provided to a third peak broadener; and
- in an eighth mode, an effluent from the third peak broadener is provided to the mass spectrometer for isotope ratio mass spectrometry without the effluent from the gas chromatography column being provided as an input to the third peak broadener; and
- wherein the effluent from the third peak broadener is provided to the mass spectrometer for isotope ratio mass spectrometry after the effluents from the first and second peak broadeners are provided to the mass spectrometer for isotope ratio mass spectrometry.

18. An isotope ratio mass spectrometry system, comprising:
- a gas chromatography column, configured to receive a sample for analysis by injection; and
- a switching arrangement, arranged to receive an effluent from the gas chromatography column, the switching arrangement having a selectable configuration, such that: in a first mode, the effluent from the gas chromatography column is provided as an input to a peak broadener; and in a second mode, an effluent from the peak broadener is provided to a mass spectrometer for isotope ratio mass spectrometry without the effluent from the gas chromatography column being provided as an input to the peak broadener.

19. The isotope ratio mass spectrometry system of claim 18, wherein the mass spectrometer comprises an ion source, configured to receive effluent from the switching arrangement and generate ions for analysis from the received effluent.

20. The isotope ratio mass spectrometry system of claim 19, wherein the mass spectrometer further comprises an ion storage device, arranged to receive ions generated by the ion source and store the received ions.

21. The isotope ratio mass spectrometry system of claim 18, wherein the peak broadener comprises a reservoir volume through which gas flows, the reservoir volume provided by a tube or flask.

22. The isotope ratio mass spectrometry system of claim 18, wherein the switching arrangement comprises a plurality of switching devices.

23. The isotope ratio mass spectrometry system of claim 22, wherein the plurality of switching devices each comprise a multi-port switching valve or a Deans' switch configuration.

24. The isotope ratio mass spectrometry system of claim 22, wherein each switching device has first and second inputs and first and second outputs; and
- wherein in a first arrangement, the first input is coupled to the first output and second input is coupled to the second output and in a second arrangement, the first input is coupled to the second output and second input is coupled to the first output.

25. The isotope ratio mass spectrometry system of claim 24, wherein the first switching device is configured to receive an effluent from the gas chromatography column as its first input and a buffer gas source as its second input, its first output being coupled to the input of the peak broadener.

26. The isotope ratio mass spectrometry system of claim 25, wherein the second switching device is coupled to the second output of the first switching device as its first input and an output of the peak broadener is provided as its second input, its first output being coupled to a sample input of the mass spectrometer and its second output being coupled to a waste line.

27. The isotope ratio mass spectrometry system of claim 18, wherein the mass spectrometer comprises an orbital-trapping type mass analyzer.

* * * * *